United States Patent [19]
Ryan, Jr. et al.

[11] Patent Number: 5,965,823
[45] Date of Patent: Oct. 12, 1999

[54] SPECIMEN HOLDER FOR THERMAL MECHANICAL TESTING MACHINE

[75] Inventors: Kenneth P. Ryan, Jr., Weymouth; Donald Hassett, Cambridge, both of Mass.; Ernest Chin, Columbia, Md.

[73] Assignee: The United States of America as represented by the Secretary of the Army, Washington, D.C.

[21] Appl. No.: 08/701,316

[22] Filed: Aug. 22, 1996

[51] Int. Cl.$^6$ .................................................. G01N 3/02
[52] U.S. Cl. ............................................................ 73/860
[58] Field of Search .............................. 73/860, 833, 853

[56] References Cited

U.S. PATENT DOCUMENTS

| | | |
|---|---|---|
| 1,428,868 | 9/1922 | Ueckert . |
| 2,350,060 | 5/1944 | Montgomery . |
| 2,368,900 | 2/1945 | Templin . |
| 2,563,881 | 8/1951 | Steadman ............................. 73/833 X |
| 3,057,032 | 10/1962 | Harding ...................................... 24/250 |
| 3,309,918 | 3/1967 | Scott et al. ................................. 73/833 |
| 3,324,714 | 6/1967 | Simon et al. ............................. 73/833 |
| 3,358,498 | 12/1967 | Wright ....................................... 73/860 |
| 4,073,185 | 2/1978 | Griffin ........................................ 73/833 |
| 4,343,190 | 8/1982 | Denko et al. .......................... 73/860 X |
| 4,393,716 | 7/1983 | Clark et al. ............................ 73/860 X |
| 4,641,534 | 2/1987 | Schneider et al. ........................ 73/856 |
| 4,874,156 | 10/1989 | Goldswerg .............................. 269/158 |
| 4,915,273 | 4/1990 | Allen ..................................... 224/30 A |
| 5,195,378 | 3/1993 | Ferguson ................................... 73/790 |
| 5,337,614 | 8/1994 | Jiang et al. ............................ 73/833 X |

FOREIGN PATENT DOCUMENTS

| | | | |
|---|---|---|---|
| 210478 | 4/1968 | U.S.S.R. .................................. 73/853 |
| 325539 | 3/1972 | U.S.S.R. .................................. 73/860 |

OTHER PUBLICATIONS

*Universal Testing Instruments Catalog 1–5–1* "Jaws and Testing Fixtures for use with Instron Universal Testing Instruments and other Tensile Testing Machines", 12 pages, Inston Engineering Corporation.

*The Gleeble Newsletter*, Duffers Scientific, Inc., Fall 1990, mailed Oct. 5, 1990, 2 pages.

Gleeble ® 1500 (Brochure from Duffers Scientific, Inc.) 5 pages published, by Aug. 1996.

*Primary Examiner*—Thomas P. Noland
*Attorney, Agent, or Firm*—Paul S. Clohan, Jr.; U. John Biffoni

[57] ABSTRACT

A test specimen holder for positioning a test specimen while protecting the hands and fingers of the user. In accordance with the present invention, a test specimen holder is provided having a main body with a handle portion located to the side of the main body. An adjustable fixed block and a spring-biased slidable blocking are provided in the main body. A pair of legs are disposed on opposite sides of the slidable and fixed blocks. A free space is provided between the two legs into which the test specimen fits and is engaged by the slidable and fixed blocks. The slidable and fixed blocks are provided with a variety of engagement surfaces, such as flat surfaces for planar specimens and notched surfaces having V-shaped grooves for cylindrical specimens. In operation, a test specimen is placed between the slidable and fixed blocks and held in place by the spring-biased slidable block holding the specimen against the fixed block. The entire specimen and specimen holder assembly is held by the handle portion of the main body and positioned between the movable and fixed jaws of the thermal mechanical testing machine. The movable jaw is moved along a testing machine jaw axis so as to engage with the test specimen and hold it in place against the fixed jaw. Once the specimen is properly engaged by the jaws, the holder device is gripped by the handle portion and pressed in the direction of a block axis transverse to the axis defined by the jaws. This compresses the springs biasing the movable block. As a result, the spacing between the slidable and fixed blocks is increased. The specimen holder can then be lifted up by the handle portion in a direction corresponding to a third axis transverse to the jaw axis and block axis until it disengages and clears the specimen. The holder is then removed from the testing zone and the specimen is left properly positioned between the testing machine jaws, ready to be tested.

6 Claims, 2 Drawing Sheets

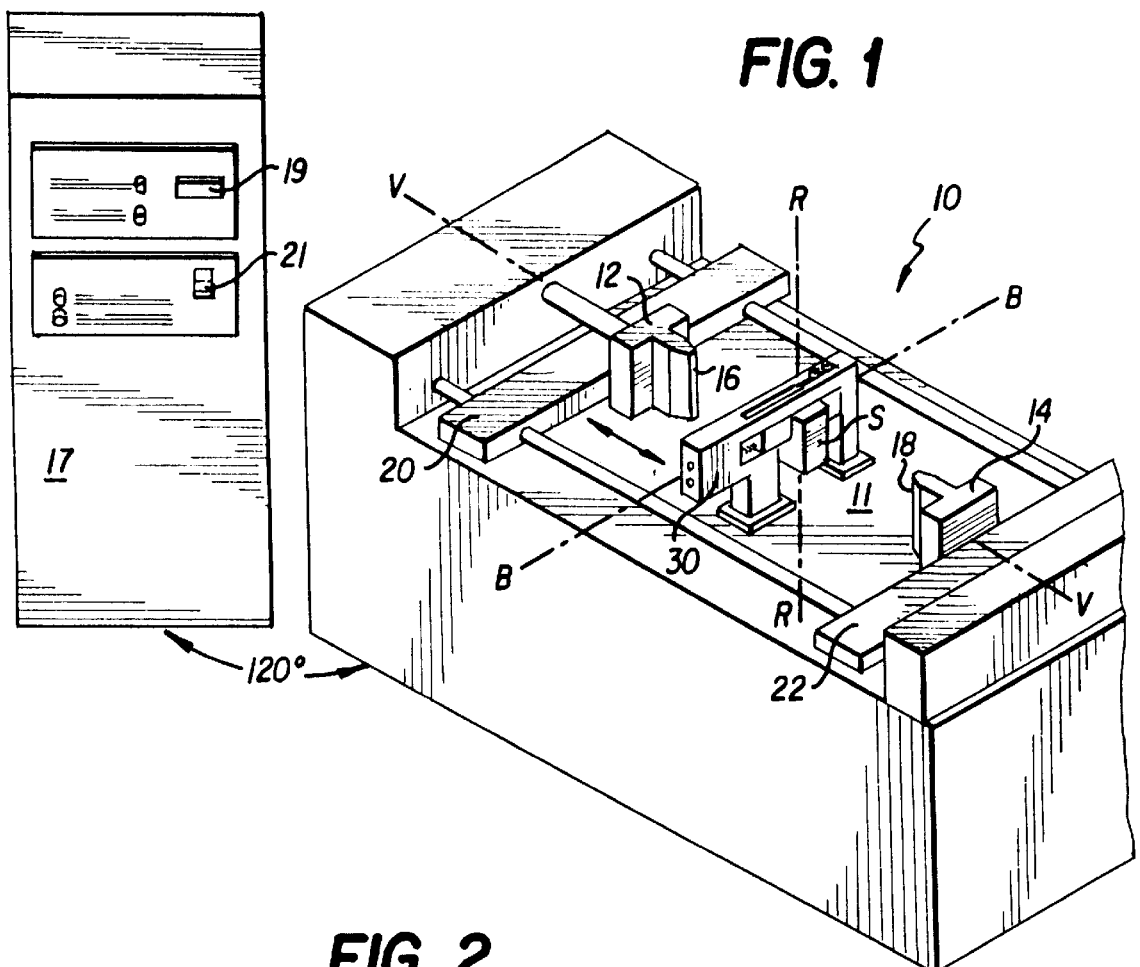
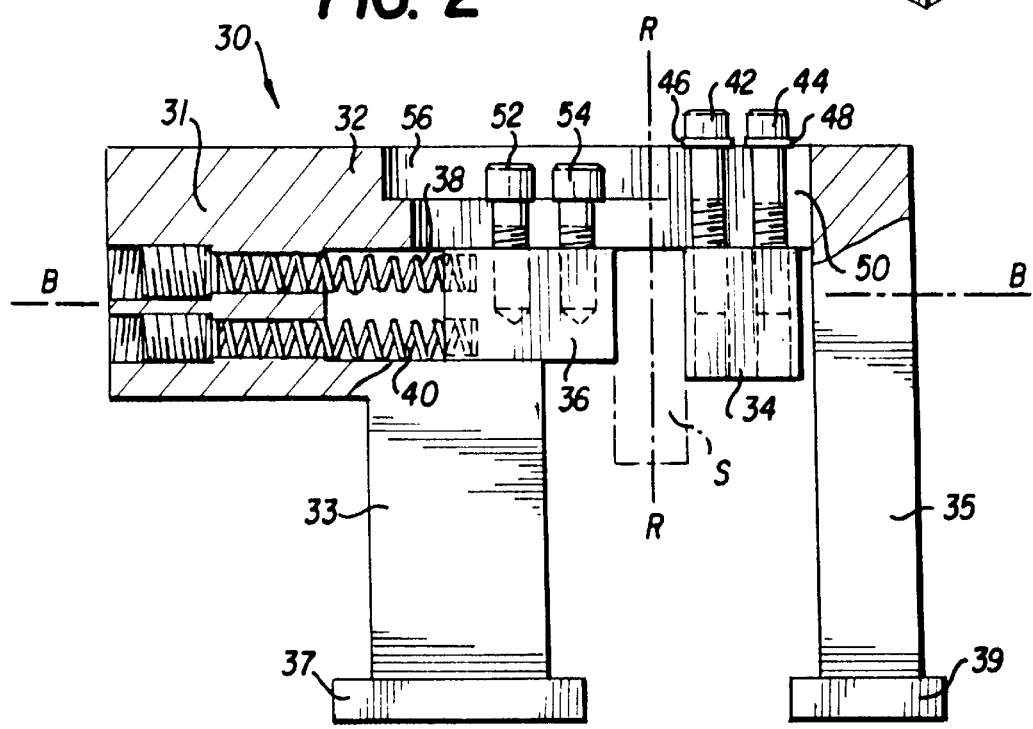

SPECIMEN HOLDER FOR THERMAL MECHANICAL TESTING MACHINE

FIELD OF THE INVENTION

The present invention is related to a specimen holder for a thermal mechanical testing device having movable jaws for engaging a specimen to be tested.

BACKGROUND OF THE INVENTION

Apparatus for performing thermal mechanical testing of test specimens are known in the art. One such well-known machine is the Gleeble, manufactured by Duffers Scientific, Inc. located in Poestenkill, N.Y. The details of such a machine are disclosed in U.S. Pat. No. 5,195,378 issued to Ferguson, the disclosure of which is hereby incorporated by reference. The Gleeble has a testing zone in a testing station which is located adjacent to and displaced from peripheral equipment, including a control panel which actuates hydraulically operated jaws which grip the specimen to be tested. The Gleeble has a pair of jaws which engage with the specimen to be tested. One of the jaws is stationary, while the other is movable. The specimen to be tested is placed between the jaws and held in place until the movable jaw is moved to engage the specimen. The movable jaw of the Gleeble are intended to impart a significant force to the test specimen, thereby imparting a test strain to the specimen. In order to place the specimen properly between the jaws, it must be held in place while the movable jaw is moved toward the stationary jaw of the apparatus and contacts the specimen. The specimen may be of various shapes, such as planar or cylindrical. Thus, it will be readily recognized that maintaining the specimen in a proper position and orientation is critical.

The operation of the hydraulic jaws is controlled from the control panel which is located adjacent to, but displaced from the testing station portion of the testing machine. As a result, for single operator operation, the operation must hold the specimen in place with one hand while operating the jaw control buttons of the control panel with the other hand. Because the control panel is displaced from the testing station and typically oriented at an angle of about 120° to the testing station, in operating the controls with one hand to move the movable jaw, the operator must look away from the testing station, while holding the specimen in the other hand.

In the past, in order to avoid possible injury to the fingers and heads of the Gleeble operator, the specimen was typically held in place by hand held tongs needle-nose pliers or other implements. This proved unsatisfactory, as the proper positioning and orientation of the specimen was difficult. As a result, it has become increasingly apparent that an improved specimen holder was desired, which would protect the user while still providing accurate positioning of the test specimen and being readily removed from the testing machine once the specimen is positioned.

There are various prior art holders and clamps for holding specimens. For example, U.S. Pat. Nos. 2,350,060 and 2,368,900 are directed to a compression testing jig having opposing T-shaped jaws which hold a specimen to be tested. The jig is not removable while the specimen is being tested. U.S. Pat. No. 1,428,868 is directed to a ring chuck having opposing spring biased jaws. U.S. Pat. No. 4,874,156 is directed to a vise having a spring biased jaw slidably engaging a fixed jaw. The vise is mounted so as to be released and moved to another work station. U.S. Pat. No. 4,915,273 is directed to a bow and gun holder having fixed and spring-biased holding plates. U.S. Pat. No. 3,057,032 is directed to a clamp for holding a flexible foam specimen for tensile testing having cam actuated spring biased gripping jaws for holding the specimen. U.S. Pat. No. 4,641,534 is directed to a holding device for aligning/holding tablet shaped specimens, the device having opposing jaws which can be spring-biased and are vertically movable for placing the specimen in a testing station.

None of these prior art devices provides ready ease of accurate alignment of a specimen between jaws of a testing machine, while also permitting ready removable of the holder by hand, while avoiding exposing the user's hand to the testing zone.

SUMMARY OF THE INVENTION

The test specimen holder in accordance with the present invention is directed to overcoming the positioning difficulties of the prior art, while protecting the hands and fingers of the user. In accordance with the present invention, a test specimen holder is provided having a main body with a handle portion located to the side of the main body. An adjustable fixed block and a spring-biased slidable blocking are provided in the main body. A pair of legs are disposed on opposite sides of the slidable and fixed blocks. A free space is provided between the two legs into which the test specimen fits and is engaged by the slidable and fixed blocks. The slidable and fixed blocks are provided with a variety of engagement surfaces, such as flat surfaces for planar specimens and notched surfaces having V-shaped grooves for cylindrical specimens.

In operation, a test specimen is placed between the slidable and fixed blocks and held in place by the spring-biased slidable block holding the specimen against the fixed block. The entire specimen and specimen holder assembly is held by the handle portion of the main body and positioned between the movable and fixed jaws of the Gleeble machine. The movable jaw is moved along a testing machine jaw axis so as to engage with the test specimen and hold it in place against the fixed jaw. Once the specimen is properly engaged by the jaws, the holder device is gripped by the handle portion and pressed in the direction of a block axis transverse to the axis defined by the jaws. This compresses the springs biasing the movable block. As a result, the spacing between the slidable and fixed blocks is increased. The specimen holder can then be lifted up by the handle portion in a direction corresponding to a third axis transverse to the jaw axis and block axis until it disengages and clears the specimen. The holder is then removed from the Gleeble and the specimen is left properly positioned between the two Gleeble jaws, ready to be tested.

The advantages of the present invention are shown in the drawings and the detailed description which follows.

BRIEF DESCRIPTION OF THE DRAWINGS

FIG. 1 is a perspective view of a thermal mechanical testing device with a testing specimen insertion device holding a specimen to be engaged between the testing jaws of the testing machine;

FIG. 2 is a front elevational view in partial section of a testing specimen insertion device in accordance with a first embodiment of the present invention;

DETAILED DESCRIPTION OF THE INVENTION

Figure 3:
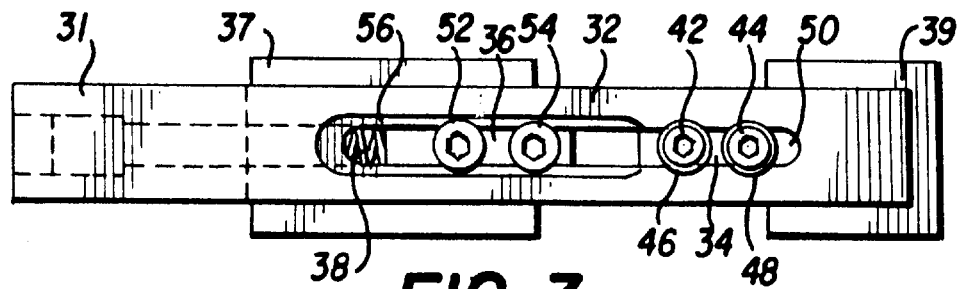
FIG. 3 is a top view of the testing specimen insertion device in accordance with the first embodiment of the present invention.

Referring now to the drawings, wherein like elements are designated by like numerals, FIG. 1 shows a perspective view of a thermal mechanical testing machine 10 of the Gleeble type. The thermal mechanical testing machine 10 having a specimen receiving portion or testing zone 11 includes a pair of opposed anvil jaws 12, 14 having respective contact surfaces 16, 18. The jaw 12 is mounted on a hydraulically operated linear motion device 20. Jaw 14 is fixed. This mounting of the jaws 12, 14 permits the jaws to move along a jaw axis V to engage a specimen S to be tested for thermal and/or mechanical stresses. An insertion device 30 is shown holding the specimen S in place for engagement by jaws 12, 14. The control panel 17 is shown located adjacent to and displaced from the specimen receiving portion 11 of testing machine 10.

FIGS. 2 and 3 show insertion device 30 comprising a main body 32 having a handle portion 31 and legs 33, 35, with respective bases 37, 39, a fixed block 34, a slidable block 36, biased along block axis B by compression springs 38, 40 disposed within main body 32. Fixed block 34 is held in place by adjusting bolts 42, 44 having washers 46, 48, respectively, and disposed within slot 50. Slidable block 36 is held slidably in place with bolts 52, 54 in recessed slot 56. Springs 38, 40 bias slidable block 36 toward fixed block 34 so as to hold a planar specimen S.

Figure 4:
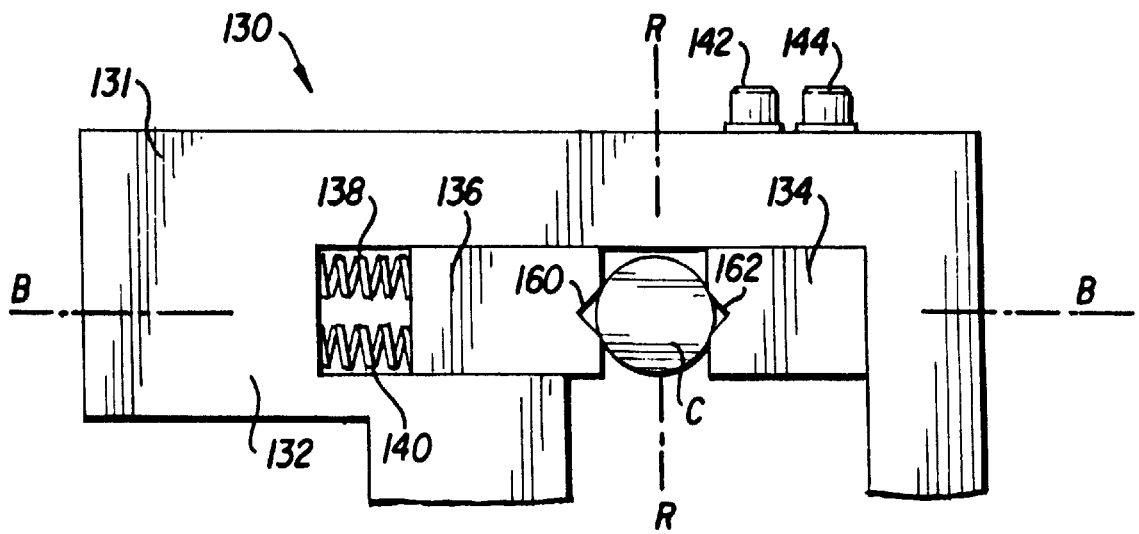
FIG. 4 is a front elevational view of a testing specimen insertion device in accordance with a second embodiment of the present invention.

FIG. 4 shows a second embodiment of an insertion device 130 having fixed block 134 and slidable block 136, biased by springs 138, 140. Slidable block 136 is movably disposed in main body 132. Main body 132 has handle portion 131. Fixed block 134 is held in place by bolts 142, 144. V-shaped grooves 160, 162 are provided respectively in slidable block 136 and fixed block 134, so as to hold a cylindrical specimen C in place between the two blocks.

Insertion device 30 is preferably made of aluminum, but may be made of any suitable material for holding a specimen to be tested.

In operation, a test specimen S is placed between the slidable and fixed blocks 36, 34 and held in place by the spring-biased slidable block 36 holding the specimen S against the fixed block 34. The entire insertion device 30 is held by the operator in one hand by the handle portion 31 of the main body 32 and positioned between the movable and fixed jaws 12, 14 of the Gleeble machine 10. The control panel 17 is operated by the operator using the other hand to actuate the auto button 19 and air ram switch 21 such that the movable jaw 12 is moved so as to engage with the test specimen S and hold it in place against the fixed jaw 14. Once the specimen S is properly engaged by the jaws 12, 14, the insertion device 30 is gripped by the handle portion 31 and pressed in the direction transverse to the axis defined by the jaws 12, 14. This compresses the springs 38, 40 biasing the movable block 36. As a result, the spacing between the slidable and fixed blocks 36, 34 is increased. The specimen holder 30 can then be lifted up by the handle portion 31 upward in the direction of removal axis R until it disengages and clears the specimen S. The holder 30 is then removed from the Gleeble and the specimen S is left properly positioned between the two Gleeble jaws 12, 14, ready to be tested. As will be seen, the insertion device 30 is configured to permit ready handling by the user without having to place his hand above or between the jaws. While the insertion device 30 is shown being used with a Gleeble type thermal mechanical testing machine, it will be readily recognized by those skilled in the art that the device may be used to releasably hold specimens for other types of machines and applications.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A specimen holder for holding a specimen to be engaged by jaws of a testing machine, said holder comprising:

means for holding the specimen comprising a fixed block and an adjustable spring biased slideable block which engage the specimen along a first axis;

a space defined by said holding means oriented such that the specimen is engageable by the jaws of the testing machine along a second axis transverse to the first axis, said space defined such that said holding means is disengageable from the specimen by said holder being moved vertically upward in a direction corresponding to a third axis transverse to the first and second axes; and handle portion means for grasping the holder by hand, said grasping means displaced from the second axis so as to be grasped without the hand of a user passing through or over the second axis.

2. A specimen holder as in claim 1, wherein said handle portion means can be gripped by one hand and the specimen disengaged by movement of the holder in a direction corresponding to the second axis and removed by movement of the holder in a direction corresponding to the third axis.

3. A specimen holder as in claim 1, wherein the blocks are contoured to engage specimens of various shapes.

4. A specimen holder as in claim 1, wherein the blocks have planar surfaces for engaging planar specimens.

5. A specimen holder as in claim 1, wherein the blocks have V-shaped notched grooves for engaging cylindrical specimens.

6. A specimen holder as in claim 1, wherein the first, second and third axes are oriented so as to prevent interference between the holder and the testing machine during insertion of the specimen and removal of the holder once the specimen is engaged by the testing machine.

* * * * *